United States Patent [19]

Lukens, Jr.

[11] 3,959,650

[45] May 25, 1976

[54] METHOD FOR DETECTING AND IDENTIFYING ALLERGY

[75] Inventor: Herbert R. Lukens, Jr., La Jolla, Calif.

[73] Assignee: Intelcom Rad Tech, San Diego, Calif.

[22] Filed: Aug. 26, 1974

[21] Appl. No.: 500,641

[52] U.S. Cl. ............................ 250/303; 250/302; 424/1; 424/7
[51] Int. Cl.² ..................................... G01T 1/161
[58] Field of Search ............... 250/303, 302; 424/1, 424/7, 8

[56] References Cited
UNITED STATES PATENTS

| | | | |
|---|---|---|---|
| 1,816,026 | 7/1931 | Schaffer | 424/8 |
| 1,891,348 | 12/1932 | Ellinger et al. | 250/302 |
| 3,449,488 | 6/1969 | Bozicevich | 424/12 |
| 3,654,090 | 4/1972 | Schuurs et al. | 424/12 |
| 3,678,148 | 7/1972 | Caiola | 250/302 |
| 3,720,760 | 3/1973 | Bennich | 250/303 |
| 3,789,116 | 1/1974 | Kay | 424/8 |
| 3,826,619 | 7/1974 | Bratu et al. | 424/1 |
| 3,853,987 | 12/1974 | Dreyer | 424/8 |
| 3,867,517 | 2/1975 | Ling | 424/1 |

*Primary Examiner*—Harold A. Dixon
*Attorney, Agent, or Firm*—Fitch, Even, Tabin & Luedeka

[57] ABSTRACT

A method is described for determining the presence of an antigen-specific antibody in a vertebrate. Effluvial tissue is exposed to antigens from known sources and is subsequently examined to detect the presence or absence of a conjugate compound formed between a particular antigen and an antibody constituent of the tissue sample. The antigen may be labeled with a fluorescent or radioactive moiety to assist in the detection of conjugate compound formation.

6 Claims, No Drawings

METHOD FOR DETECTING AND IDENTIFYING ALLERGY

This invention relates generally to the detection of antibodies in vertebrates and, more particularly, to a method for determining the presence of an antigen-specific antibody in a vertebrate.

The detection of antibodies in vertebrates is used for a number of purposes including the diagnosis of allergies and for various medical and biological research purposes. Although a variety of methods are currently used for detecting antibodies, many of these methods may be unsatisfactory or inconvenient.

For example, in the diagnosis for allergies in humans, typical diagnostic tests currently in use are clinical and involve either scratching, puncturing or other intradermal form of contact of antigens and the subsequent observations of the traumatized area for reactions. This, of course, requires the presence of the patient as well as results in some considerable degree of discomfort, while also presenting a danger of infection and even possibly overreaction as a result of extreme sensitivity.

It is an object of the present invention to provide an improved method for determining the presence of an antigen-specific antibody in a vertebrate.

Another object of the invention is to provide a reliable in vitro diagnostic test for allergy.

Another object of the invention is to provide a method for determining the presence of an antigen-specific antibody in a vertebrate which does not require observation of clinical symptoms in the vertebrate.

Other objects of the invention will become apparent to those skilled in the art from the following description.

Very generally, the method of the invention involves the obtaining of a sample of effluvial tissue from the vertebrate and the exposure of the sample to the specific antigen the antibody for which is being investigated. The conditions of exposure are such as would allow the formation of a conjugate compound of the specific antigen and the corresponding antibody in the event such antibody is present. Presence or absence of the conjugate compound is then detected. In the description herein and in the appended claims, the term "antigen" is intended to include a complete antigen formed by the uniting of a hapten with a protein, as well as an antigen which is complete initially.

Antigens are substances of large molecules, such as proteins, some starches and some oils, and which can result in the production of antibodies in a vertebrate and unite with such antibodies to produce an observable reaction. Some substances of smaller molecules including certain chemicals and drugs may be capable of combining with a protein to become a complete antigen. Such substances are typically known as haptens or incomplete antigens. In either case, the union of an antibody and an antigen or a hapten, may introduce a series of observable events, such as allergy symptoms. Antibodies which are specifically capable of uniting with such antigens are defined herein as antigen-specific antibodies. It is the uniting of an antigen-specific antibody with its specific antigen that produces the allergic reaction. In the foregoing definition, it is assumed that the haptens are included, since the bonding of a hapten with a protein results in an antigen.

In practicing the method of the invention, a sample of effluvial tissue or extract thereof is obtained from the vertebrate. The effluvial tissue utilized is that which is most convenient or easily available, such as hair, nail, and skin scraping. To insure the accuracy of the method, it may be desirable to clean the sample such as by flushing or scraping.

The sample is then exposed to a specific antigen from a known source under conditions such as would allow the formation of a conjugate compound thereof in the presence of the antigen's specific antibody. The uniting of the antigen with its antigen-specific antibody, as previously mentioned, produces the observable reaction. Accordingly, the detection of such a conjugate compound will indicate the presence of the antigen-specific antibody. This exposure may be accomplished by immersing the sample in a solution containing the specific antigen or a hapten which forms the specific antigen.

In detecting the presence or absence of the mentioned conjugate compound, any suitable test may be used. For example, the antigen may be tagged or labeled with a fluorescent or radioactive moiety to assist in the detection. It is typically necessary to thoroughly rinse the tissue after exposure to the antigen solution in order to insure the removal of any unfixed tagged antigen. It may also be desirable to dry the tissue before examining it to detect the presence or absence of the conjugate compound.

In the detection and identification of allergies by the method of the invention, the antigens or haptens may include pollens, fungi, molds, bacteria, seeds, nuts, spices, garden plants, vegetables, fruits, cereals, grasses, weeds, wildflowers, ivy, beans, berries, cotton, or substances derived therefrom. Such animal substances as fish, shellfish, feathers, hooves, nails, hair, fur, dander, epithelia, insects or insect parts, animal emanations, wool, meat products, and dairy products or substances derived therefrom, may also be used. The antigens or haptens may also include various mineral, agricultural, medicinal and/or industrial substances, such as pharmaceuticals, dyes, tars, adhesives, monomers, polymers, disinfectants, pesticides, fungicides, herbicides, resins, chromium or chromium compounds, nickel or nickel compounds, mercury or mercury compounds, iodine or iodine compounds, and other inorganic substances or substances derived therefrom.

Although the method of the invention has been described herein in connection with allergy diagnosis, the determination of the presence of an antigen-specific antibody in a vertebrate may be desirable for other purposes. For example, certain research needs may necessitate the determination of the presence of specific antibodies in animals. Also, the method of the invention may be used as a qualitative and/or quantitative analysis of samples for specific antigens.

The following examples are provided as a showing that the method of the invention is capable of successfully selecting allergic individuals, and it is not intended that the invention be limited thereby.

Example 1

Hair from two persons, only one of whom was allergic to Bermuda grass, was obtained and cleaned by scraping the root ends with a steel blade. The root ends were then immersed for one hour in a solution of the antigen, Bermuda grass allergen extract, tagged with fluorescein isothiocyanate. The hairs were then removed from the solution, rinsed ten times in pure distilled water, air dried, and mounted on separate labeled microscope slides. Each slide was examined with a microscope while excited with filtered light of less than five thousand angstroms from a mercury lamp for fluorescence of greater than five thousand angstroms. Only the hair from the person allergic to Bermuda grass exhibited the characteristic greenish fluorescence from the fluorescent moiety used in the experiment. Hair from the person who was not allergic to Bermuda grass did not exhibit the characteristic fluorescence of the fluorescent moiety.

Example 2

Hair from two persons, one of whom was allergic to a Southern California weed, was obtained and cleaned by scraping the root ends with a steel blade. A mixture of extracts of Southern California weeds was tagged with fluorescein isothiocyanate and the clean hairs immersed in the solution for one hour. The hairs were then removed from the solution, rinsed ten times in pure distilled water, air dried, and mounted on separate labeled microscope slides. Each was examined with a microscope while excited with a filtered light of less than five thousand angstroms from a mercury lamp for fluorescence of greater than five thousand angstroms. Only those hairs from the allergic person were fluorescent, whereas hair from the person who was not allergic did not exhibit the characteristic fluorescence.

It may be seen, therefore, that the invention provides a novel method for determining the presence of an antigen-specific antibody in a vertebrate. The method is applicable to the diagnosis of allergies in humans as an in vitro diagnostic test, as well as being applicable to other situations in which detection of such antigens or haptens is desired.

Various modifications of the invention in addition to those shown and described herein will become apparent to those skilled in the art from the foregoing description. Such modifications are intended to fall within the scope of the appended claims.

What is claimed is:

1. A method for determining the presence of an antigen-specific antibody in a vertebrate, comprising, obtaining a sample of effluvial tissue from the vertebrate, providing a specific antigen for the antibody being investigated labeled by means of a moiety, exposing said sample to the specific antigen under conditions such as would allow the formation of a conjugate compound thereof in the presence of the antigen-specific antibody, rinsing the sample to remove excess moiety, and detecting the presence or absence of the conjugate compound by detecting the presence or absence of the moiety.

2. A method according to claim 1 wherein the labeling moiety is fluorescent.

3. A method according to claim 2 wherein the labeling moiety is fluorescein isothiocyanate.

4. A method according to claim 1 wherein the labeling moiety is radioactive.

5. A method according to claim 1 wherein said method comprises an in vitro diagnostic test for allergy.

6. A method according to claim 1 wherein the labeling moiety is fluorescein isothiocyanate, and wherein the conjugate compound is detected by microscope while the sample is excited with filtered light of less than five thousand angstroms wave length.

* * * * *